(12) United States Patent
Brown et al.

(10) Patent No.: US 10,849,779 B2
(45) Date of Patent: Dec. 1, 2020

(54) POSTURE IMPROVEMENT DEVICES AND METHODS FOR USE

(76) Inventors: Timothy W. Brown, Laguna Beach, CA (US); William Schultz, Santa Ana, CA (US); Robert Waeger, Santa Ana, CA (US); Mark Spitaleri, Santa Ana, CA (US)

( * ) Notice: Subject to any disclaimer, the term of this patent is extended or adjusted under 35 U.S.C. 154(b) by 948 days.

(21) Appl. No.: 12/126,338

(22) Filed: May 23, 2008

(65) Prior Publication Data

US 2009/0062704 A1  Mar. 5, 2009

Related U.S. Application Data (60) Provisional application No. 60/931,581, filed on May 23, 2007, provisional application No. 61/023,380, filed on Jan. 24, 2008.

(51) Int. Cl.
*A61F 5/37* (2006.01)
*A61F 5/02* (2006.01)
*A41D 13/00* (2006.01)

(52) U.S. Cl.
CPC .......... *A61F 5/026* (2013.01); *A41D 13/0015* (2013.01)

(58) Field of Classification Search
CPC .... A61F 5/026; A61F 5/02; A61F 5/00; A61F 5/022; A61F 5/024; A61F 5/028; A61F 5/03; A61F 5/34; A61F 5/3746; A41D 13/0015; A41D 13/0531; A41D 13/1245; A41D 13/00; A41B 2400/38
USPC ...... 128/874, 875, 873, 845; 602/19, 20, 32, 602/36; 2/44
See application file for complete search history.

(56) References Cited

U.S. PATENT DOCUMENTS

| | | | |
|---|---|---|---|
| 846,562 A * | 3/1907 | Grayson | |
| 1,231,011 A * | 6/1917 | Glasgow | A41C 3/00 2/44 |
| 3,663,797 A | 5/1972 | Marsh | |
| 5,306,229 A | 4/1994 | Brandt et al. | |
| 5,344,384 A | 9/1994 | Ostrow et al. | |
| 5,555,566 A | 9/1996 | Kuhn | |
| 5,819,322 A * | 10/1998 | Dicker | A41D 13/0015 2/456 |
| 5,829,058 A * | 11/1998 | Dicker | A41D 13/0015 2/69 |
| 5,857,990 A | 1/1999 | Maas | |
| 5,937,442 A * | 8/1999 | Yamaguchi | A41D 13/0015 2/115 |
| 6,176,816 B1 | 1/2001 | Dicker et al. | |
| 6,306,111 B1 | 10/2001 | Dean | |

(Continued)

*Primary Examiner* — Victoria J Hicks
(74) *Attorney, Agent, or Firm* — Buchalter, a professional corp.; Kari L. Barnes (57) ABSTRACT

A posture improvement device provides neuromuscular stimulation or proprioceptive therapy using a combination of pressure, torque and angle simultaneously applied to a user in order to train body muscles for proper posture through muscle memory. The device is a garment designed to be worn by the user, which is preferably configured like a short-sleeved undershirt or T-shirt. The garment may be fabricated of a stretchable, yet taut material in order to provide the desirable form-fitting feature such that pressure may be readily applied to the surface of the skin for neuromuscular stimulation. This elastomeric material is also preferably breathable and/or which has moisture wicking capabilities.

13 Claims, 5 Drawing Sheets

(56) References Cited

U.S. PATENT DOCUMENTS

| | | |
|---|---|---|
| 6,440,094 B1 | 8/2002 | Maas |
| 6,464,656 B1 * | 10/2002 | Salvucci et al. |
| 6,936,021 B1 * | 8/2005 | Smith .......................... 602/19 |
| 6,945,945 B2 | 9/2005 | Givler et al. |
| 7,037,281 B1 | 5/2006 | Jeffrey et al. |
| 7,037,284 B2 | 5/2006 | Lee |
| 7,134,969 B2 | 11/2006 | Citron et al. |
| 7,516,498 B2 | 4/2009 | Torry |
| 7,871,388 B2 * | 1/2011 | Brown ................... A61F 5/026 |
| | | 602/19 |
| 9,009,863 B2 | 4/2015 | Decker |
| 2002/0143373 A1 | 10/2002 | Courtnage et al. |
| 2003/0130603 A1 * | 7/2003 | Minne ................ A41D 13/0531 |
| | | 602/19 |
| 2005/0197607 A1 * | 9/2005 | Brown ................... A61F 5/026 |
| | | 602/19 |
| 2008/0208089 A1 * | 8/2008 | Newkirk et al. ................ 602/19 |
| 2015/0264980 A1 | 9/2015 | Tally |

* cited by examiner

POSTURE IMPROVEMENT DEVICES AND METHODS FOR USE

This application claims the benefit under 35 U.S.C. 119(e) of the filing dates of each of Provisional U.S. Application Ser. No. 60/931,581, entitled Posture Improvement Devices and Methods for Use, filed on May 23, 2007, and Provisional U.S. Application Ser. No. 61/023,380, entitled Posture Improvement Devices and Methods for Use, filed on Jan. 24, 2008.

This application is also related to co-pending utility application Ser. No. 10/795,656, filed on Mar. 8, 2004 and commonly assigned herewith. This prior application was published as U.S. Patent Application Publication No. 20050197607 on Sep. 8, 2005.

All of the above identified prior applications are herein expressly incorporated by reference, in their entirety.

BACKGROUND OF THE INVENTION

The present invention relates generally to body mechanics and, more particularly, to posture improvement devices configured to be worn on a user's torso and which are specifically adapted to improve the user's body alignment or posture through the use of neuromuscular stimulation.

The importance of good posture is well known among health professionals. Posture generally refers to the alignment of the body and, more specifically, to the relative static and dynamic positioning of the body and its limbs. Ideally, in a body exhibiting good posture, the spine has no lateral curvature and the legs have little angulation in the knees and ankles. In addition, when viewed from the side, the spine forms a slight S-shape with the two curves of the S-shape being evenly disposed on opposite sides of an imaginary line extending downwardly from the head through the body's center. Such an alignment provides an even distribution of body weight over the spine and lower body joints resulting in a relatively uniform distribution of pressure on the intervertebral discs of the spine.

The effects of poor posture are well documented and include limited range of motion wherein muscles, such as the pectoral muscles in the chest, may be permanently shortened due to a hunched-over upper body position. Other effects of poor posture include discomfort in the form of headaches at the base of the skull and pain in the shoulders, arms, and hands. Additionally, poor posture may lead to pain in the jaw due to a forward-head position, as well as decreased lung capacity due to decreased volume of the chest cavity and lungs. One of the most common consequences of poor posture is the onset of lower back pain which may increase with advancing age. Finally, a hunched-over upper body position of poor posture can add years to one's appearance.

However, by assuming good posture, gravitational forces may be more evenly distributed through the bones, ligaments and muscles of the body. Maintaining good posture is equally important during passive (static) activities such as sitting and standing, as well as during dynamic activities such as walking, running, and lifting. Theoretically, the slight S-shape of the spine that is characteristic of good posture should preferably be maintained during both static and dynamic activities. Unfortunately, our increasingly sedentary lifestyle, wherein many hours are spent sitting in front of a computer, driving an automobile, or watching television, has an adverse effect on posture. Such static activities may result in forward protrusion of the head and neck, rounding of the thoracic and lumbar spine and stretching of the spinal ligaments. Such stretching gradually causes pain in the neck and upper back and results in fatiguing of the body's muscles and ligaments. Poor posture during dynamic activities such as running and lifting results in inefficient body movements with increased stress on muscles and ligaments.

Maintaining an awareness of proper posture during static and dynamic activities may sometimes prevent overstressing of muscles and ligaments. In addition, maintaining an awareness of proper posture may train certain muscles through muscle memory such that proper posture eventually becomes a habit. However, it is sometimes difficult to maintain an awareness of proper posture during mentally challenging activities such as working at a computer, or during physically challenging activities such as participating in aggressive sports. Physical therapists may utilize postural therapy to improve the posture of a patient. Such postural therapy may include techniques such as shoulder taping and breathing exercises. Conventional chiropractic techniques may utilize body manipulation and treatment to help keep the patient's spine in alignment. However, the patient must take the time and energy to visit the offices of a physical therapist or a chiropractor in order to receive the needed postural therapy and/or chiropractic manipulation. Moreover, alternative treatment, such as cutaneous nerve stimulation, is often overlooked as a method to improve the patient's posture.

As can be seen, there exists a need in the art for a device that is specifically adapted to continuously train and develop certain body muscles such that the user's posture may be improved. In addition, there exists a need in the art for a device that allows for developing such muscle training during static activities such as standing and sitting. In addition, there exists a need in the art for a device that discretely allows for developing such muscle training during dynamic activities such as walking, running and during other daily activities. Furthermore, there exists a need in the art for a device for improving the user's posture that may be progressively adjusted in accordance with changes or improvements in the user's posture over time. Finally, there exists a need in the art for a device for improving the user's posture that may be adjusted according to varying physiological parameters between users including differences in user's age, body size, muscular development and underlying pathophysiologic status.

SUMMARY OF THE INVENTION

The invention is a posture improvement device that is specifically adapted to provide neuromuscular stimulation or proprioceptive therapy using a combination of pressure, torque and angle simultaneously applied to the user in order to train body muscles for proper posture through muscle memory. The device comprises a garment designed to be worn by a user and which is adapted to envelop at least a portion of the user's torso and at least a portion of the user's upper arms. This garment is preferably configured like a short-sleeved undershirt or T-shirt, wherein, as is well known in the art, the posterior and anterior portions of the shirt together cover substantially all of the wearer's torso.

Pressure is applied to the user's skin in order to proprioceptively stimulate cutaneous nerve receptors of the skin by configuring the garment as a relatively tight, form-fitting shirt. The garment is adapted to envelop at least a portion of the user's torso and at least a portion of the user's upper arms. The garment has an inner and an outer surface, a front side, a back side, opposing lateral sides, and a pair of partial sleeves. The front side includes a chest portion and a stomach portion, while the back side includes a back portion. The garment also defines opposing shoulder portions and a waist portion extending about a lower end of the garment. A short-sleeved version of the garment allows for effective training of the user's pectoralis major muscles located in the user's chest. In addition, the short-sleeved configuration of the garment enhances the user's range of motion, particularly at the shoulder joints, in addition to providing conditioning of the user's rotator cuffs.

The garment may be fabricated of a stretchable, yet taut material in order to provide the desirable form-fitting feature such that pressure may be readily applied to the surface of the skin for neuromuscular stimulation. In this regard, the garment is preferably fabricated of elastomeric material that is also preferably breathable and/or which has moisture wicking capabilities such as may be provided by a material comprised of a combination of Lycra and Spandex.

More particularly, there is provided a garment for proprioceptively treating a wearer, which comprises an anterior portion and a posterior portion joined to the anterior portion. Each of the anterior portion and the posterior portion are fabricated of a thin, elastomeric material which is form-fitting, in order to apply pressure to the surface of the wearer's skin to enhance neuromuscular stimulation thereto. As noted above, and in the drawings, the posterior and anterior portions together cover substantially all of the wearer's torso. A proprioceptive panel is integrated with the posterior garment portion and positioned to extend over the upper back or inter scapular region of the wearer. The proprioceptive panel is fabricated of an elastomeric material and having characteristics which cause the garment to stimulate optimal scapular position. In one embodiment, the proprioceptive panel is comprised of the same elastomeric material as the posterior portion. In an alternative embodiment, the proprioceptive panel is comprised of a heavier, more dense elastomeric material than that comprising a remainder of the posterior portion.

In some embodiments of the present invention, the inventive garment further comprises an elastic band disposed on the proprioceptive panel. This elastic band is fabricated of a stronger elastomeric material than that comprising the proprioceptive panel, and is positioned to substantially coincide with the inferior medial border of the wearer's scapula.

In a presently preferred embodiment of the present invention, the proprioceptive panel is positioned to extend along substantially an entire length of the spine of the wearer.

The inventive garment preferably further comprises at least one and preferably a plurality of shoulder strap portions positioned to extend from the proprioceptive panel upwardly and over the wearer's shoulder toward the garment anterior portion. The shoulder strap portion is integrated with the remainder of the garment posterior portion and is comprised of elastomeric material.

In one embodiment, the proprioceptive panel is generally triangular in shape, positioned to extend downwardly from the shoulders of the wearer toward an apex positioned to be disposed at approximately the small of the wearer's back.

Preferred embodiments of the invention further comprise at least one and preferably a plurality of arm strap portions extending from the proprioceptive panel and positioned to proceed about an arm of the wearer toward the anterior portion of the garment. The arm strap portions are integrated with the garment posterior portion and are comprised of elastomeric material. Nerve receptor stimulators are preferably disposed on an inner surface of the garment, for contacting the wearer's skin and creating additional proprioceptive stimulation when the garment is worn. These nerve receptor stimulators preferably comprise a plurality of strategically placed neuro nubs, comprising soft, tacky bumps and extending inwardly from the inner surface of the garment. Alternatively, the nerve receptor stimulators may comprise proprioceptive viscoelastic pads.

In preferred embodiments, the material comprising each of the anterior and posterior portions also comprises a moisture wicking material. The proprioceptive panel is stitched to the posterior portion, though it may also be joined by alternative methods as well. One possibility is to integrate the panel into the posterior portion of the garment by blending it into the base material forming the posterior portion, using advanced production techniques, forming a single, seamless, composite layer.

In another aspect of the invention, there is disclosed a method of making a garment for proprioceptively treating a wearer. This method comprises a step of joining a posterior portion to an anterior portion of the garment together, wherein each of the posterior portion and the anterior portion are comprised of a thin, elastomeric material, so that the joined posterior and anterior portions form a garment resembling a shirt. The method further comprises a step of joining a proprioceptive panel, comprised of an elastomeric material, to the posterior portion, in a location wherein when the garment is worn by a user, the proprioceptive panel is disposed over at least a portion of the user's spine and inter scapular region. These steps may be performed in interchangeably, as they are not sequence dependent. In one presently preferred embodiment, the joining steps are performed by stitching the posterior portion and the anterior portion together, and stitching the proprioceptive panel to the posterior portion. In some embodiments, the proprioceptive panel comprises a second layer of material over the base material forming the posterior portion. In other embodiments, the proprioceptive panel is integrated with the posterior portion in such a manner that only a single layer of material results.

The invention, together with additional features and advantages thereof, may be best understood by reference to the following description taken in conjunction with the accompanying illustrative drawings. In these accompanying drawings, like reference numerals designate like parts throughout the figures.

DETAILED DESCRIPTION OF THE INVENTION

Figure 1:
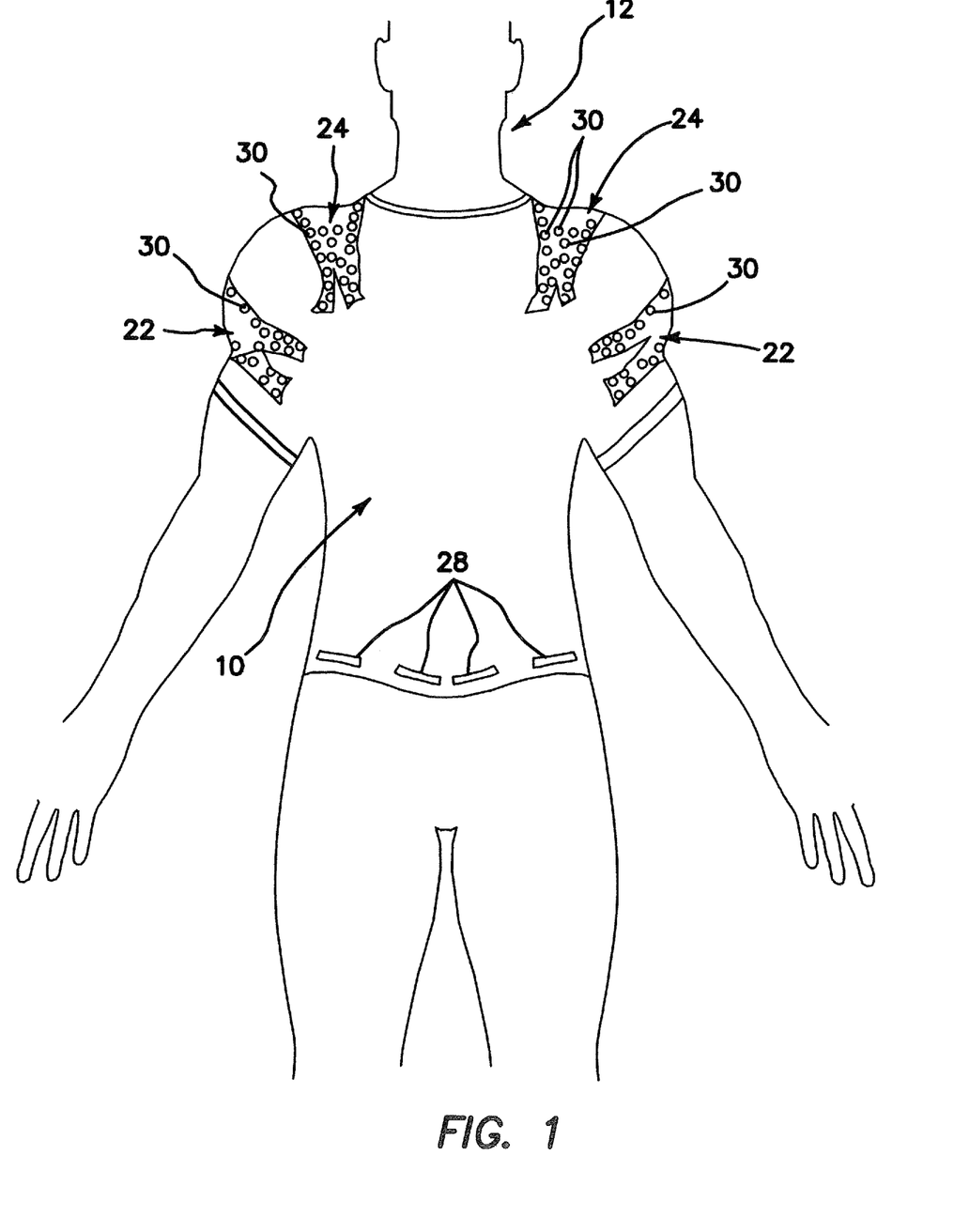
FIG. 1 is an anterior view of an embodiment of the garment of the present invention, being worn by a user.
Figure 2:
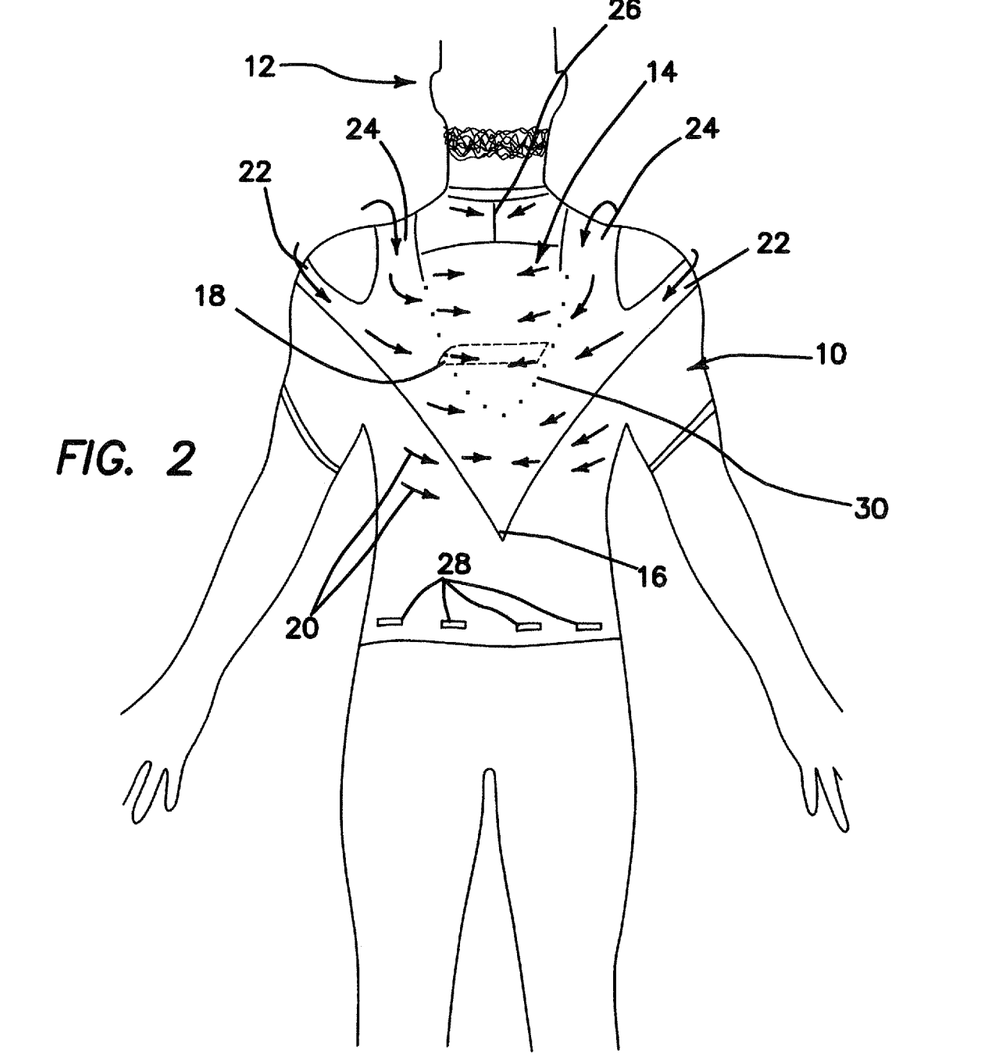
FIG. 2 is a posterior view of the garment of FIG. 1.

Referring now to the drawings, wherein the showings are for purposes of illustrating the present invention and not for purposes of limiting the same, FIGS. 1 and 2 are views of a first embodiment of a posture improvement garment 10, which is configured to be worn by a user 12 and which is configured to envelop at least a portion of the user's torso and at least a portion of the user's upper arms. In this regard, the garment 10 is generally configured to be similar to one of a short-sleeved undershirt, T-shirt, or polo shirt. While the illustrated garment 10 is designed as a "pull-over" style, the garment may also be provided with an open or partially open front or back portion, which is selectively closeable by means of known garment closure systems, such as a zipper, buttons, snaps, and the like. Such a style eases the wearability of the garment because it can be put on or removed without pulling the garment over one's head.

The embodiments illustrated in the aforementioned '656 application have been shown to have a remarkable proprioceptive therapeutic effect on the wearer, substantially improving his/her posture and relieving pain related to poor posture and related muscle strain. However, the illustrated embodiments in that application are not particularly adapted for use in casual recreational and social settings, or for routine retail sale to consumers. Because of the external strapping, if they are to be worn in such settings, aesthetics dictate that they be worn under external garments, which must be relatively bulky and heavy to adequately cover the therapeutic garment. Accordingly, the present invention performs many of the same functions as the prior embodiments disclosed in the '656 application without the use of external strapping. Similar proprioceptive effects are achieved by the use of strategically placed stretch panels and proprioceptive pads, integrated directly into the material used to fabricate the garment. As a result, the garments of the present invention are particularly suited for the consumer market, as they are attractive and comfortable.

Regarding material from which the garment 10 may be fabricated, it is preferred that the material be thin, and have an elastic quality that stretches or moves with the user's body, in order to provide a desirable form-fitting feature such that pressure may be readily applied to the surface of the user's skin in order to enhance neuromuscular stimulation thereto. The material may contain, but not be limited to, polyester, spandex, elastic, nylon, and the like. It may have metal ions woven into it, or other mechanical sweat wicking, temperature regulating materials which are known in the art and function in an equivalent way to regulate temperature and wick moisture. Its breathability and/or moisture wicking capabilities function to improve the user's comfort level during periodic wearing of the device 10.

Referring particularly to FIG. 2, there is shown a elastic stretch panel or proprioceptive posture patch 14. As shown, the patch 14 is generally triangular in shape (its border is represented by the dotted outline in the drawing), and is welded or sewn into the upper back, or inter scapular region, extending downwardly from both shoulders of the user 12 to a point 16 disposed at the small of the user's back. The proprioceptive posture patch 14 is fabricated of an elastic material, which may be the same as that from which the garment 10 is fabricated, or it may alternatively be a heavier, more dense elastic material to assist in support of relatively weak middle or lower trapezious, rhomboid, and serratus musculature respectively. The purpose of the patch 14 is to stimulate optimal scapular position. This is the functional base for optimal posture and scapular kinematics. The patch may be disposed as a second layer atop the base layer of the garment, or may alternatively be blended (integrated) into the garment material, using suitable production techniques, to form a single composite layer.

In a preferred embodiment, an elastic band 18 is employed in about the midpoint of the patch 14, which is fabricated of stronger elastic than that used for the patch 14. The band 18 is positioned to substantially coincide with the inferior medial border of the scapula.

As demonstrated by the arrows 20, the base layer of the garment 10 has a posterior (retracting) directional influence on the body of the user 12.

Referring now to FIG. 1, as well as FIG. 2, two upper arm straps 22 and two shoulder straps 24 begin on the anterior side of the garment 10 (FIG. 1) and continue around to the posterior side, as shown (FIG. 2). These straps 22, 24 are built into the garment 10, in much the same way as the patch 14. The arm straps 22 are designed to provide a specific directional pull on the infraspinatus and teres minor muscles. The shoulder straps 24 are designed to influence problems relating to posterior scapular tilt, in part by influencing the pectoralis minor muscle adjacent to the coracoid process.

Darts 26 (FIG. 2) may be used to enhance posterior pull/cue to help the scapula to attain an optimal position.

As can be seen in each of FIGS. 1 and 2, viscoelastic tape 28 may be disposed about the hem of the garment 10, for the purpose of preventing migration of the garment. Alternative means providing a tacky surface for contacting the user's skin may instead be used.

It should be noted that the specific angles of arrows shown in FIG. 2 may indicate coupled motion influence upon the axis of the scapula, caused by the various elastomeric elements of the garment 10.

Figure 2A:
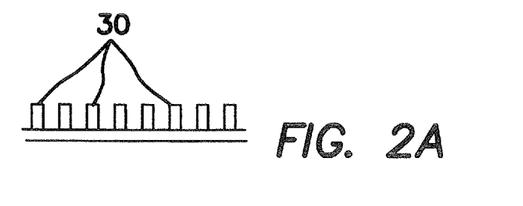
FIG. 2A is a side view of a section of neuro nubs for use with the garments of the invention.

The various dots 30 shown in FIGS. 1 and 2 are neuro nubs. These neuro nubs are more particularly shown in FIG. 2A. These neuro nubs 30 preferably comprise soft, tacky bumps, or cutaneous nerve receptor stimulators, which are designed to provide a massaging, stimulating effect when the user moves. As shown, these nubs 30 are disposed on each of the straps 22 and 24, where they stimulate portions of the body adjacent to rotator cuff muscle attachment points on the humerus, as well as pectoralis minor muscles in the vicinity of the coracoid process. In general, the inventor has found that patterns of such neuro nubs 30 are helpful in creating proprioceptive stimulation, and also function to provide decreased migration of the garment 10 as the body moves throughout its full range of motion. They are disposed at specific areas on the inside surface of the garment, to stimulate cutaneous nerve receptors in the skin and soft tissue structures to enhance "noise" that creates cues to the brain, enhancing muscle balance, body position awareness, posture, function, and performance.

Desired locations of the neuro nubs 30 are at known acupuncture sites, as stimulation of these specific energy meridians enhances blood flow and stimulates normal physiology to organs and soft tissues that supply movement, support, and information crucial to those seeking optimal health and function.

Although one elastic panel 18 and four elastic straps 22, 24 are shown in the embodiment of FIGS. 1 and 2, a plurality of such panels 18 and/or straps 22, 24, of various shapes and sizes, may be employed if desired. As noted, the stretch panels 18 and straps 22, 24 may be constructed of the same or similar materials as the garment 10 or patch 14. The panels 18 and straps 22, 24 function to stimulate muscles that are too tight (the panels/straps will stretch these muscles), or too loose and undertoned (the panels/straps will add tone to these muscles and encourage/stimulate them to work). Conventional approaches to date have focused on mechanical support systems that have been shown to create atrophy and a reliance on a brace, which in the long term can create a system of dependence that the inventor believes is detrimental to optimal health and efficient recovery and performance. The elastic or stretch panels/straps as well as the patch(es) 14, on the other hand, create specific traction and tactile stimulation of cutaneous nerves in the skin. There are a minimum of 20,000 of such nerves per square inch of skin that will transfer specific information to the receptors (mechanoreceptors/nociceptors) that exist by the thousands/millions in the muscle, tendon, ligament, and joint surfaces, causing a predictable unloading of specific, predictable and common muscle imbalances that create and perpetuate joint stress and injury throughout the body.

Figure 3:
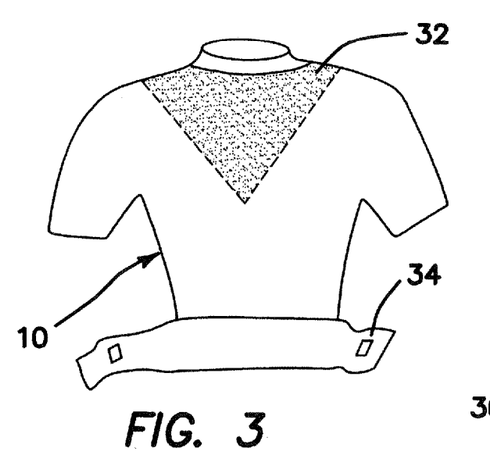
FIGS. 3-5 are sequential views of another embodiment of a garment of the present invention, illustrating a sequence of fabrication of the garment to include the advantageous posture-improving features of the invention.
Figure 4:
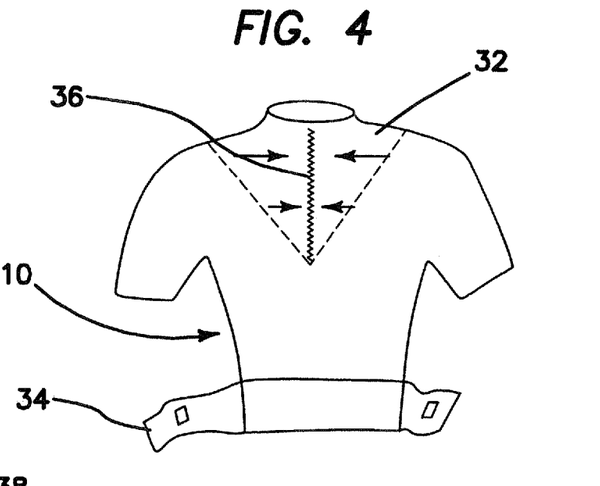
Figure 5:
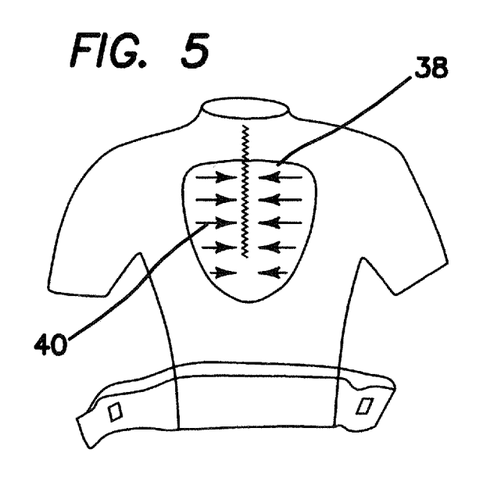
Figure 6:
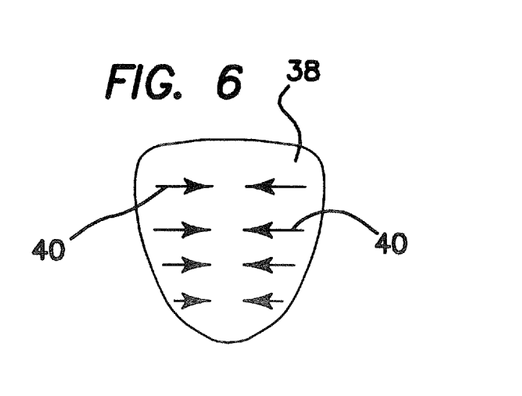
FIG. 6 is a view, in isolation, of a specific tension elastic posture patch for use in fabricating the garment of FIGS. 3-5.

Now referring to FIGS. 3-6, there is shown a somewhat modified embodiment of the garment 10 of the invention. The posterior side of the garment is shown. The views in FIGS. 3-5 are sequential, wherein, as shown in FIG. 3, a V 32 has been cut out of the shirt. In this embodiment of the invention, an optional belt or strap 34 is provided at the base of the garment 10. As shown in FIG. 4, the edges of the V 32 have been sewn together along seam 36. Then for additional support, an elastic posture patch 38 is applied over the seam 36 as shown. The elastic patch 38 is adapted to apply specific tension along arrows 40 to assist the user's posture, as discussed above.

Figure 7:
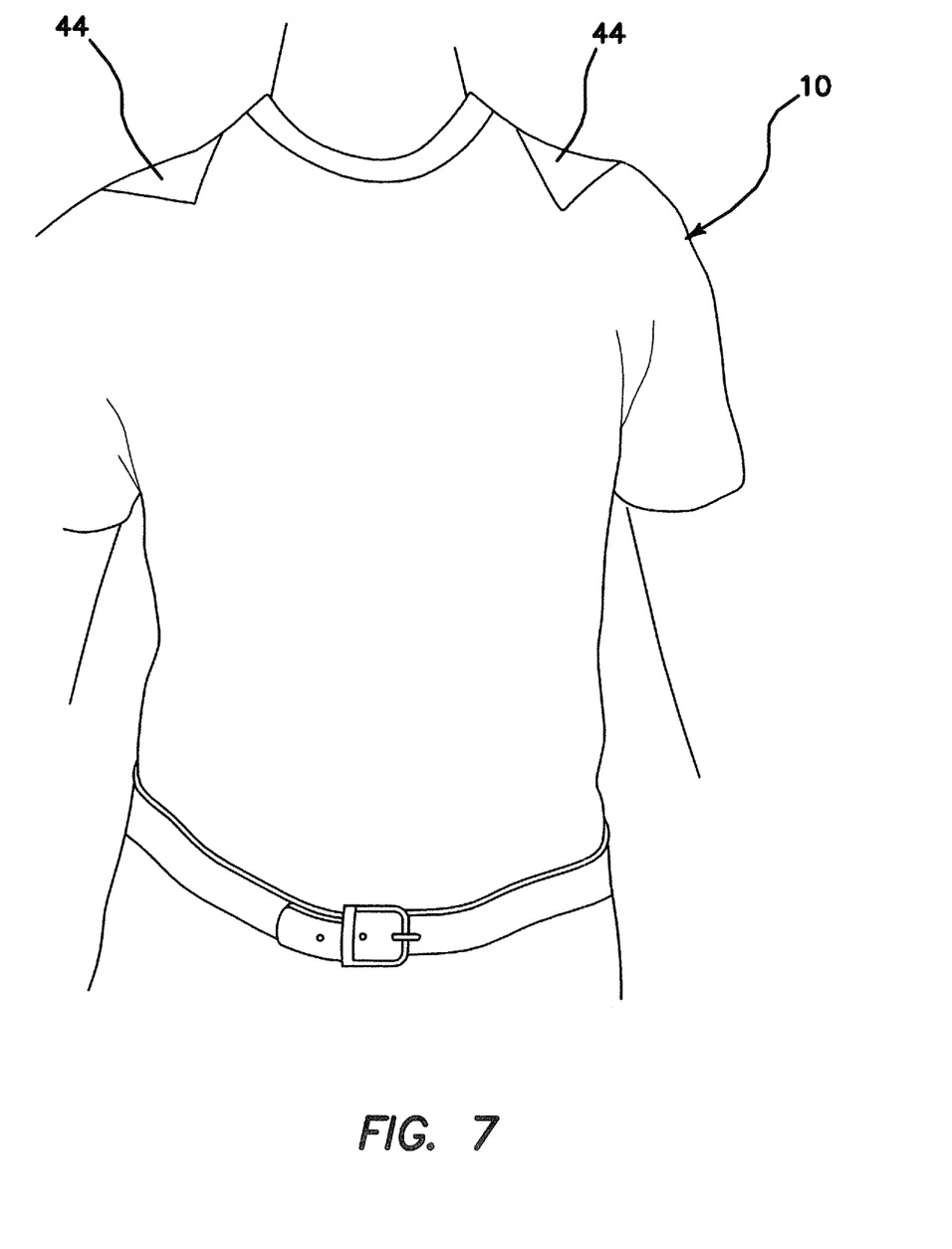
FIG. 7 is an anterior view of still another embodiment of a garment of the present invention.
Figure 8:
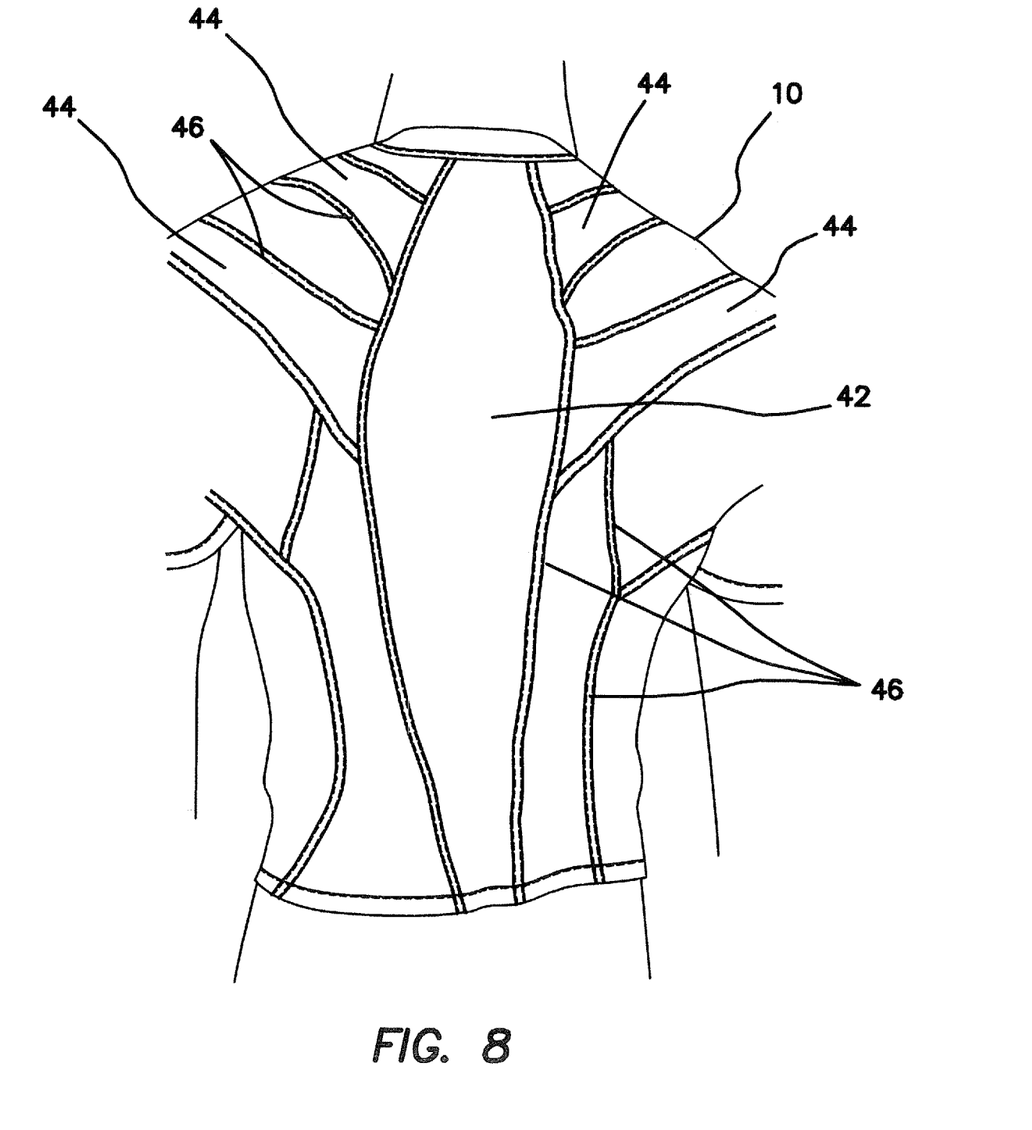
FIG. 8 is a posterior view of the embodiment of FIG. 7.

Still another, presently preferred, embodiment of the garment 10 of the invention is illustrated in FIGS. 7 and 8. This embodiment is similar in many respects to the prior embodiments, but employs an elastic or stretch band or panel 42 which extends along substantially the entire length of the spine of the wearer, as shown in FIG. 8. Straps 44 are also provided, which extend, as shown, from the patch 42 up and over each shoulder of the user. The straps 44 preferably extend over the shoulder and onto the anterior side of the garment, as shown in FIG. 7. The panels 42, 44 are integrated into the remainder of the garment 10 by stitching 46.

The resulting garment for proprioceptively treating at least a portion of a torso of a wearer may therefore have an anterior portion being configured to form fit an anterior area of the torso of the wearer, a posterior portion joined to the anterior portion, the posterior portion being configured to form fit a posterior area of the torso of the wearer and being sized smaller than the anterior portion, a proprioceptive panel, the proprioceptive panel being formed of a same material across the entire proprioceptive panel forming a single elongated strip and being positioned to extend over an upper back region of the torso of the wearer, and a plurality of straps, each strap integrated with said garment and having a first end attached to the proprioceptive panel and a second end attached to the anterior portion. The garment may also have a neck opening, and at least four straps where a first two straps couple the proprioceptive panel to the anterior portion and a second two straps couple the proprioceptive panel to the anterior portion on an opposite side of the neck opening as the first two straps. The second end of each strap may be attached to the anterior portion at a location in the upper body region of the garment such that the second end of each strap is configured to be positioned over a wearer's chest when the garment is worn by a wearer. The straps may further be configured to attached at one end to the anterior portion at a location in the upper body region when worn by the wearer and at the other end to the proprioceptive panel positioned adjacent a user's spine when the garment is worn by the wearer. This configuration has been found to substantially increase and enhance the cues which proprioceptively stimulate the user's brain and body to a corrected posture.

Another example of the garment for a torso of a wearer may also have an anterior portion being configured to form fit an anterior area of the torso of the wearer, a posterior portion joined to the anterior portion, the posterior portion being configured to form fit a posterior area of the torso of the wearer, a proprioceptive panel, and a first pair of straps, and a second pair of straps. The proprioceptive panel may be integrated with said posterior portion and be positioned to extend over an upper back region of the torso of the wearer. Each strap of the first pair of straps may be integrated with said garment and may have a first end attached to the proprioceptive panel and a second end attached to the anterior portion. Each strap of the second pair of straps may be integrated with said garment and may have a first end attached to the proprioceptive panel and a second end attached to the anterior portion. The proprioceptive panel, first pair of straps, and second pair of straps may be integrated with the garment by being sewn into the posterior portion. The first pair of straps may extend directly from the proprioceptive panel up and over a shoulder of the wearer in a worn position, and the second pair of straps may extend directly from the proprioceptive panel up and over an other shoulder of the wearer in a worn position. The first pair of straps may directly couple to the proprioceptive panel on a first side of the proprioceptive panel and the second pair of straps directly couple to the proprioceptive panel on a second side of the proprioceptive panel opposite the first side. A portion of the posterior portion of the garment may be positioned between the first pair of straps, and another portion of the posterior portion of the garment may be positioned between the second pair of straps. The proprioceptive panel may extend across and between the first a pair of straps and the second pair of straps such that a continuous connection is made from one strap of the first pair of straps across the wearer through the proprioceptive panel to one strap of the second pair of straps, wherein across is laterally across the wearer's torso in the worn position. The proprioceptive panel, the first pair of straps, and the second pair of straps comprise a more dense elastic material than a remainder of the garment.

Significantly, in all of the illustrated embodiments, the posterior panel of the shirt is smaller than the anterior panel (which are sewn together), preferably by about two inches. This increases the retractive pull of the shirt, and thus the compression applied to the user's skin.

Proprioceptive viscoelastic pads may optionally be employed in each of the illustrated embodiments, on the inside surface thereof, either permanently or releasably mounted thereto, for contacting the user's skin at strategic locations in order to increase the proprioceptive effect of the garment. These pads, preferably made of silicone, have a skin-contacting surface which is grooved or otherwise modified to improve tactile response, using an acupuncture-type approach. The pressure generated by the garment 10 creates an acupressure effect. In one embodiment, two of these pads may be deployed on the chest region of the user, while two others are deployed on the scapula border, but, of course, the strategic locations and numbers of pads may be varied in accordance with specific therapeutic objectives.

To summarize, the present invention uniquely functions, due to its proprioceptive approach, to address the following conditions:

a) upper trapezium pain, b) rotator cuff weakness, by optimizing scapular position to improve the rotator cuff muscle, c) mid-thoracic pain, by decreasing tension in the periscapular muscles, d) scapular dyskinesis,
e) biceps tendinitis,
f) thoracic outlet syndrome,
g) impingement syndrome, and
h) glenohumeral instability.

Essentially, the garment of the invention functions to create an exoskeleton for the user's body, thereby allowing for the proprioceptive treatment of strategic regions. Increased pressure is applied to these strategic body regions to perform the advantageous proprioceptive treatment. Prior art approaches involved mechanical treatment, i.e. physically manipulating portions of the body to desired configurations. This modern inventive approach instead induces a nervous system response through the application of strategic proprioceptive compression. There is no attempt to physically move portions of the body.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A garment for proprioceptively treating at least a portion of a torso of a wearer, comprising:
    an anterior portion being configured to form fit an anterior area of the torso of the wearer;
    a posterior portion joined to the anterior portion, the posterior portion being configured to form fit a posterior area of the torso of the wearer;
    a proprioceptive panel, the proprioceptive panel being formed of a same material piece across the entire proprioceptive panel defining a single elongated strip and integrated with said posterior portion and being positioned to extend over an upper back region of the torso of the wearer; and
    a plurality of straps, each strap of the plurality of straps integrated with said garment and having a first end attached to the proprioceptive panel and a second end attached to the anterior portion; and further comprising a neck opening, and the plurality of straps including at least four straps where each of a first two straps directly couple the proprioceptive panel to the anterior portion and each of a second two straps couple the proprioceptive panel to the anterior portion on an opposite side of the neck opening as the first two straps, wherein each of the plurality of straps directly couple to the proprioceptive panel.

2. The garment as recited in claim 1, wherein the proprioceptive panel is comprised of a more dense material than that comprising a remainder of the posterior portion.

3. The garment as recited in claim 2, wherein the proprioceptive panel extends along a length of the garment such that the proprioceptive panel is configured to extend a length of the spine of the wearer when worn.

4. The garment as recited in claim 3, wherein an inner surface of the plurality of straps comprises nerve receptor stimulators configured to cause tactile stimulation to a surface of the wearer's skin.

5. The garment as recited in claim 4, wherein the proprioceptive panel and the plurality of straps are integrated into the garment in such a manner that only a single layer results.

6. The garment as recited in claim 5, wherein the straps are integrated into the garment by stitching.

7. The garment as recited in claim 6, wherein the posterior portion is smaller than the anterior portion.

8. The garment as recited in claim 7, wherein the second end of each strap is attached to the anterior portion at a location in the upper body region when worn by a wearer.

9. The garment as recited in claim 1, wherein the proprioceptive panel is comprised of a more dense material than that comprising a remainder of the posterior portion.

10. The garment as recited in claim 9, wherein the first end of each strap attached to the proprioceptive panel is configured to be positioned adjacent the wearer's spine when the garment is worn by the wearer and the proprioceptive panel covers an entire area between the first ends of each strap of the plurality of straps.

11. The garment as recited in claim 1, wherein said proprioceptive panel is stitched to said posterior portion.

12. The garment as recited in claim 1, wherein the proprioceptive panel and plurality of straps are configured to cause the garment to apply a retractive pull from the posterior portion corresponding to an interscapular region of the wearer toward a spine of the wearer when the garment is worn by the wearer to enhance cues to stimulate the wearer to a corrected posture.

13. The garment as recited in claim 1, wherein the proprioceptive panel is monolithic and continuous along an entire length and an entire width of the proprioceptive panel such that the proprioceptive panel extends directly between the first end of one of the plurality of straps to the first end of another of the plurality of straps on an opposite side of the proprioceptive panel than the one of the plurality of straps.

* * * * *